(12) United States Patent
Harutyunyan et al.

(10) Patent No.: US 7,719,265 B2
(45) Date of Patent: May 18, 2010

(54) METHODS FOR DETERMINING PARTICLE SIZE OF METAL NANOCATALYST FOR GROWING CARBON NANOTUBES

(75) Inventors: Avetik Harutyunyan, Columbus, OH (US); Elena Mora Fernandez, Columbus, OH (US); Toshio Tokune, Raymond, OH (US)

(73) Assignees: Honda Motor Co., Ltd. (JP); The Ohio State University Research Foundation, Columbus, OH (US)

( * ) Notice: Subject to any disclaimer, the term of this patent is extended or adjusted under 35 U.S.C. 154(b) by 1319 days.

(21) Appl. No.: 10/992,275

(22) Filed: Nov. 17, 2004

(65) Prior Publication Data
US 2006/0104889 A1    May 18, 2006

(51) Int. Cl.
G01R 33/14    (2006.01)
G01N 27/76    (2006.01)
G01R 33/035   (2006.01)

(52) U.S. Cl. .................. 324/239; 324/248; 324/228; 324/261

(58) Field of Classification Search .............. 324/201, 324/204, 228, 234, 239, 248, 262, 261, 260; 73/865.5; 977/880, 881
See application file for complete search history.

(56) References Cited

U.S. PATENT DOCUMENTS

| 5,546,986 A | 8/1996 | Clark, II et al. |
| 5,549,973 A | 8/1996 | Majetich et al. |
| 5,783,263 A | 7/1998 | Majetich et al. |
| 6,027,946 A | 2/2000 | Weitschies et al. |
| 6,401,526 B1 | 6/2002 | Dai et al. |
| 6,764,874 B1 | 7/2004 | Zhang et al. |
| 2002/0017884 A1 | 2/2002 | Ishida |
| 2002/0131910 A1 | 9/2002 | Resasco et al. |
| 2004/0005269 A1 | 1/2004 | Huang |
| 2004/0099093 A1 | 5/2004 | Harutyunyan |

OTHER PUBLICATIONS

Ibrahim et al., Determination of Particle Size Distribution in an Fe2O3-Based Catalyst Using Mangetometry and X-Ray Diffration, J. Mater Res. vol. 7, No. 7, Jul. 1992, pp. 1856-1860.*

Yakushiji et al., Composition Dependence of Particle Size Distribution and Giant Magnetoresistance in Co-Al-O Granular Films, Journal of Magnetism and Magnetic Materials, 212, 2000, pp. 75-81.*

Chantrell et al., Measurements of Particle Size Distribution Parameters in Ferrofluids, IEEE Trans. on Magnetics, vol. Mag. 14, No. 5, Sep. 1978, pp. 975-977.*

V.S. Rao, Evaluation of Particle Size Measurement Techniques for Dispersed Iron Catalysts, Energy Fuels, 1994, 8(1), pp. 44-47.*

(Continued)

*Primary Examiner*—Kenneth J Whittington
(74) *Attorney, Agent, or Firm*—Fenwick & West LLP; Mark E. Duell

(57) ABSTRACT

Methods and processes for determining the particle size distribution of metal catalysts are provides. Superconducting Quantum Interference Device (SQUID) magnetometer is used to evaluate the magnetic catalyst particle sizes dispersed in the support material. Dependence on variation of the metal/support material ratio, which defines the metal particle sizes, the catalyst can show paramagnetic, superparamagnetic, and ferromagnetic behaviors.

12 Claims, 6 Drawing Sheets

OTHER PUBLICATIONS

Pradhan et al., Finely Dispersed Iron, Iron-Molybdenum, and Sulfated Iron Oxides as Catalysts for Coprosessing Reactions, Energy and Fuels 1991, 5, 712-720.*

PCT International Search Report and Written Opinion, PCT International Patent Application No. PCT/US05/41620, May 21, 2007.

Bethune, D.S., "Cobalt Catalysed Growth of Carbon Nanotubes With Single-Atomic-Layer Walls", Nature, Jun. 17, 1993, pp. 605-607, vol. 363.

Ijima, Sumio et al., "Single-Shell Carbon Nanotubes of 1-nm Diameter", Nature, Jun. 17, 1993, pp. 603-605, vol. 363.

Ivanov, V. et al., "The Study of Carbon Nanotubules Produced By Catalytic Method", Chemical Physical Letters, Jun. 24, 1994, pp. 329-335.

Journet, C. et al., "Large-Scale Production of Single-Walled Carbon Nanotubes By The Electric-Arc Technique", Nature, Aug. 21, 1997, pp. 756-758, vol. 388.

Li, W. Z. et al., "Large-Scale Synthesis of Aligned Carbon Nanotubes", Science, Dec. 6, 1996, pp. 1701-1703, vol. 274.

Thess, Andreas et al., "Crystalline Ropes of Metallic Carbon Nanotubes", Science, Jul. 26, 1996, pp. 483-487, vol. 273.

* cited by examiner

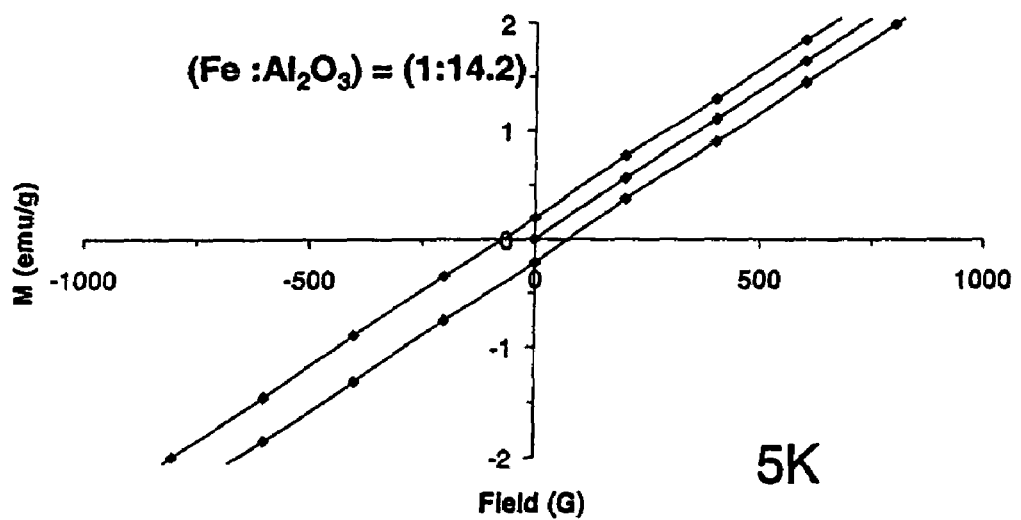
Fig. 3a
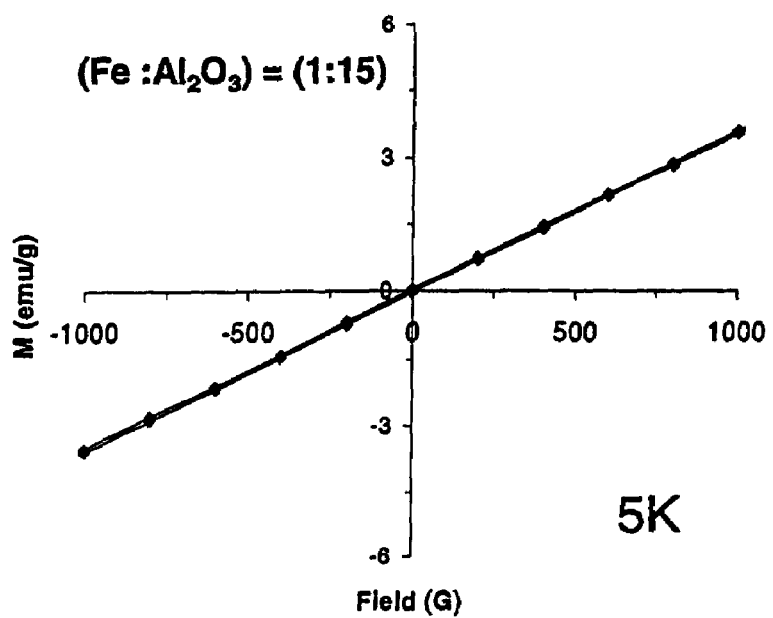
Fig. 3b
Figure 3

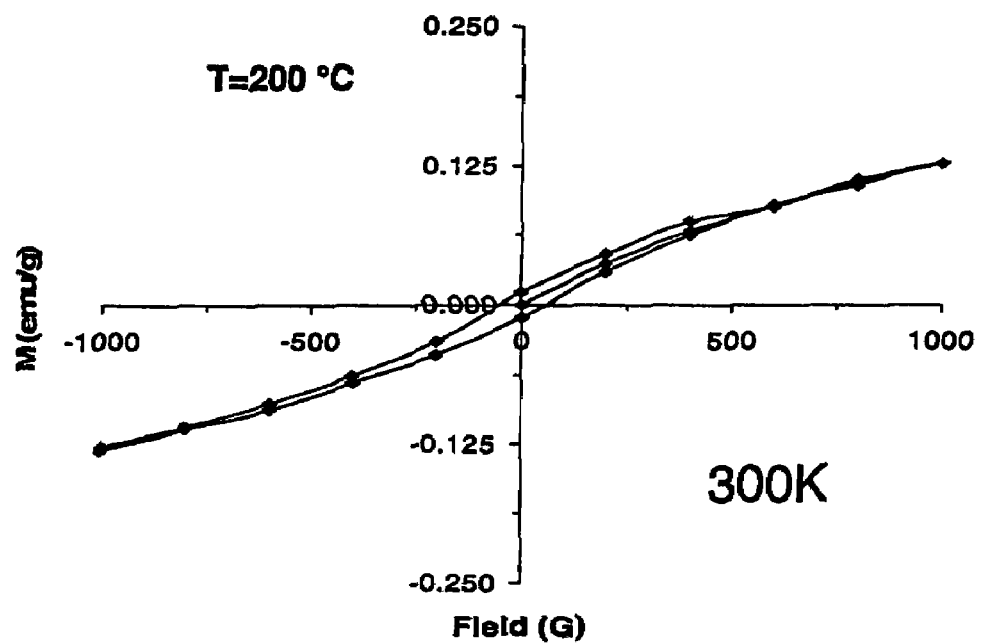
Fig. 4a
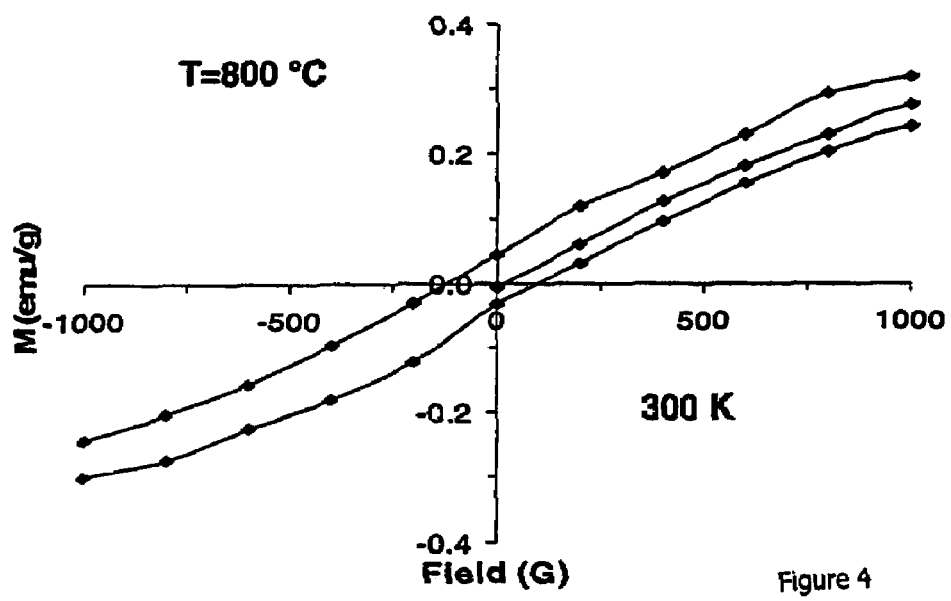
Fig. 4b
Figure 4

METHODS FOR DETERMINING PARTICLE SIZE OF METAL NANOCATALYST FOR GROWING CARBON NANOTUBES

FIELD OF INVENTION

The present invention relates to methods for the preparation (synthesis) of carbon single-walled nanotubes using chemical vapor deposition method.

BACKGROUND

Carbon nanotubes are hexagonal networks of carbon atoms forming seamless tubes with each end capped with half of a fullerene molecule. They were first reported in 1991 by Sumio Iijima who produced multi-layer concentric tubes or multi-walled carbon nanotubes by evaporating carbon in an arc discharge. They reported carbon nanotubes having up to seven walls. In 1993, Iijima's group and an IBM team headed by Donald Bethune independently discovered that a single-wall nanotube could be made by vaporizing carbon together with a transition metal such as iron or cobalt in an arc generator (see Iijima et al. Nature 363:603 (1993); Bethune et al., Nature 363: 605 (1993) and U.S. Pat. No. 5,424,054). The original syntheses produced low yields of non-uniform nanotubes mixed with large amounts of soot and metal particles.

Presently, there are three main approaches for the synthesis of single- and multi-walled carbon nanotubes. These include the electric arc discharge of graphite rod (Journet et al. Nature 388: 756 (1997)), the laser ablation of carbon (Thess et al. Science 273: 483 (1996)), and the chemical vapor deposition of hydrocarbons (Ivanov et al. Chem. Phys. Lett 223: 329 (1994); Li et al. Science 274: 1701 (1996)). Multi-walled carbon nanotubes can be produced on a commercial scale by catalytic hydrocarbon cracking while single-walled carbon nanotubes are still produced on a gram scale.

Generally, single-walled carbon nanotubes are preferred over multi-walled carbon nanotubes because they have unique mechanical and electronic properties. Defects are less likely to occur in single-walled carbon nanotubes because multi-walled carbon nanotubes can survive occasional defects by forming bridges between unsaturated carbon valances, while single-walled carbon nanotubes have no neighboring walls to compensate for defects. Defect-free single-walled nanotubes are expected to have remarkable mechanical, electronic and magnetic properties that could be tunable by varying the diameter, number of concentric shells, and chirality of the tube.

It is generally recognized that smaller catalyst particles of less than 3 nm are preferred for the growth of smaller diameter carbon nanotubes. However, the smaller catalyst particles easily aggregate at the higher temperatures required for the synthesis of carbon nanotubes. U.S. Patent Application No. 2004/0005269 to Huang et al. discloses a mixture of catalysts containing at least one element from Fe, Co, and Ni, and at least one supporting element from the lanthanides. The lanthanides are said to decrease the melting point of the catalyst by forming alloys so that the carbon nanostructures can be grown at lower temperatures.

Aside from the size of the catalyst, the temperature of the reaction chamber can also be important for the growth of carbon nanotubes. U.S. Pat. No. 6,764,874 to Zhang et al. discloses a method of preparing nanotubes by melting aluminum to form an alumina support and melting a thin nickel film to form nickel nanoparticles on the alumina support. The catalyst is then used in a reaction chamber at less than 850° C. U.S. Pat. No. 6,401,526, and U.S. Patent Application Publication No. 2002/00178846, both to Dai et al., disclose a method of forming nanotubes for atomic force microscopy. A portion of the support structure is coated with a liquid phase precursor material that contains a metal-containing salt and a long-chain molecular compound dissolved in a solvent. The carbon nanotubes are made at a temperature of 850° C.

It is well known that the diameter of the SWNTs produced is proportional to the size of the catalyst particle. In order to synthesize nanotubes of small diameter, it is necessary to have catalyst particles of small particle size (less than about 1 nm). Catalysts of small average particle sizes with narrow distribution are difficult to synthesize. Further, recognized methods for determining the catalyst particle size distribution are not currently available, especially when the catalyst particles are supported on support powders, and thus buried inside the pores of the support powders.

Thus, there is a need for methods and processes for controllable synthesis of carbon single walled nanotubes with small and narrow distributed diameters. Accordingly, the present invention provides novel methods and processes for determining the average particle size and particle size distribution of catalyst particles that can be used for preparation and optimization of catalyst and for the synthesis of SWNTs with small and narrow distributed diameters.

SUMMARY

The present invention provides methods and processes for determining the size of the catalyst particles, and/or for determining the size of the catalyst particles on support materials. The catalyst particles can be used in methods and processes for growing single-wall carbon nanotubes in high yields and with high quality.

The present invention provides methods for determining the average particle size of a metal catalyst by obtaining magnetization curve of the metal catalyst using SQUID and determining the average particle size from the magnetization curve. The metal catalyst can be a Group V metal, a Group VI metal, a Group VII metal, a Group VIII metal, a lanthanide, or a transition metal or combinations thereof. The catalyst preferably has a particle size between about 0.1 nm to about 10 nm. The catalyst can be supported on a powdered oxide, such as $Al_2O_3$, $SiO_3$, MgO and the like, herein the catalyst and the support are in a ratio of about 1:1 to about 1:50.

In another aspect, the methods involve contacting a carbon precursor gas with a catalyst on a support, wherein the catalyst has an average diameter of less than about 2 nm and wherein SWNT having narrow distribution of diameters are formed. The average particle size of a metal catalyst by obtaining magnetization curve of the metal catalyst using SQUID and determining the average particle size from the magnetization curve. The carbon precursor gas can be methane that can additionally contain other gases such as argon and hydrogen. The catalyst can be a Group V metal, a Group VI metal, a Group VII metal, a Group VIII metal, a lanthanide, or a transition metal or combinations thereof. The catalyst preferably has a particle size between about 1 nm to about 50 nm. The catalyst can be supported on a powdered oxide, such as $Al_2O_3$, $SiO_3$, MgO and the like, where the catalyst and the support are in a ratio of about 1:1 to about 1:50. Once the desired particle size of the catalyst is obtained, as determined by SQUID, they can be used for the production of SWNTs of high quality.

In another aspect, the invention provides a carbon nanotube structure produced by the process of contacting a carbon precursor gas with a catalyst on a support at a temperature between the melting point of the catalyst and the eutectic point of the catalyst and carbon. The carbon precursor gas can be methane that can additionally contain other gases such as argon and hydrogen. The catalyst can be a V metal, a Group VI metal, a Group VII metal, a Group VIII metal, a lanthanide, or a transition metal or combinations thereof. The catalyst preferably has a particle size between about 1 nm to about 15 nm. The catalyst can be supported on a powdered oxide, such as $Al_2O_3$, $SiO_3$, MgO and the like, herein the catalyst and the support are in a ratio of about 1:1 to about 1:50.

BRIEF DESCRIPTION OF DRAWINGS

FIG. 3 depicts the magnetization curves of the catalysts having different ratio of iron and the support aluminum powder. In FIG. 3a, the Fe:$Al_2O_3$ ratio is 1:14.2, and in FIG. 3b, the Fe:$Al_2O_3$ ratio is 1:15.

FIG. 4 illustrates the magnetization curves of Fe:$Al_2O_3$ having a ratio is 1:14.2 after heat treatment at 200° C. (FIG. 4a) and after heat treatment at 800° C. (FIG. 4b).

(FIG. 5a) and after heat treatment at 800° C. (FIG. 5b).

DETAILED DESCRIPTION

I. Definitions

Figure 1:
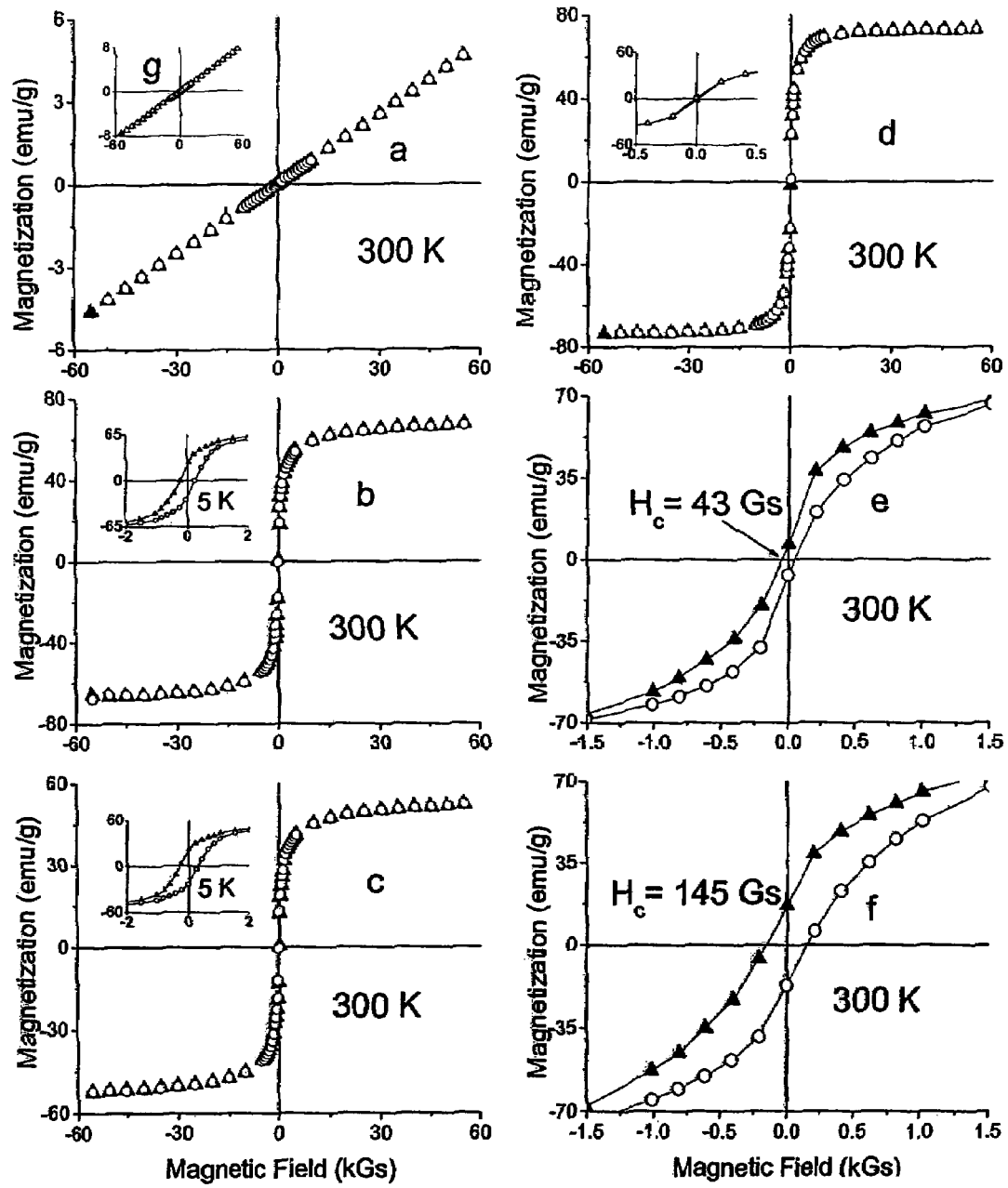
FIG. 1 provides the magnetization curves of iron nanoparticles supported with aluminum oxide powder (Fe:$Al_2O_3$) with mean diameters a) less than 1 nm, b) 5 nm and c) 9 nm and the magnetization curves of Fe:$Al_2O_3$ after they had been used for the synthesis of carbon SWNTs growth with mean catalyst diameters of d) less than 1 nm, e) 5 nm and f) 9 nm respectively. Inset shows magnetization curve for initial catalyst with mean diameter less than 1 nm, after Ar treatment at 800° C. for 90 min. Magnetization values are presented per gram of Fe.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York, and Cotton et al. (1999) "Advanced Inorganic Chemistry $6^{th}$ Ed." Wiley, N.Y.

The term "magnetic," as used hereinafter, includes all types of materials that respond to magnetic fields, such as, but not limited to, ferromagnetic, paramagnetic, and superparamagnetic materials.

The term "magnetic material" encompasses any material having at least some magnetic content and therefore includes material having an amount of magnetic material ranging from greater than 0% to 100%.

The term "ferromagnetic" as used herein refers to substances such as iron, nickel, or cobalt and various alloys that exhibit extremely high magnetic permeability, a characteristic saturation point, and magnetic hysteresis.

The term "paramagnetic" refers to a material having unpaired electron in the atoms of the material whose induced magnetization is parallel and proportional to the strength of the intensity of the magnetizing field.

The term "superparamagnetic" refers to particles with the size below which the anisotropy energy is smaller than the thermal energy. In that case, thermal fluctuations cause the magnetic moment of the domains to fluctuate randomly between their energy minima.

The terms "single-walled carbon nanotube" or "one-dimensional carbon nanotube" are used interchangeable and refer to cylindrically shaped thin sheet of carbon atoms having a wall consisting essentially of a single layer of carbon atoms, and arranged in an hexagonal crystalline structure with a graphitic type of bonding.

The term "mul "superparamagnetic" refers to particles with the size below which the anisotropy energy is smaller than the thermal energy. In that case, thermal fluctuations cause the magnetic moment of the domains to fluctuate randomly between their energy minima. ti-walled carbon nanotube" as used herein refers to a nanotube composed of more than one concentric tubes.

The terms "metalorganic" or "organometallic" are used interchangeably and refer to co-ordination compounds of organic compounds and a metal, a transition metal or metal halide.

II. Overview

The present invention discloses methods, and processes for determining the size of the catalyst particles, thereby allowing for the control of the quality of the catalyst. The catalysts thus produced can be used in the manufacture of carbon single-wall nanotubes (SWNT) and structures using the carbon vapor deposition method. The catalyst produced by the inventive methods provides high yield and high quality of carbon SWNTs.

The invention provides methods and processes for determining the size distribution of particles, particularly metal catalysts on support material. According to the invention, SWNT of preselected diameter distribution can be produced by contacting a carbon-containing gas with a catalyst supported on a support. The catalyst particles are synthesized to have a narrow range of diameter. The diameter of the catalyst particles, with or without support, can be evaluated by using SQUID magnetometer, and the catalyst synthesis process (variation of metal/support ratio) can be continued until catalyst particles having a narrow range of diameters are obtained. The catalyst thus obtained can be contacted with a carbon-containing gas at a temperature sufficient to decompose the carbon-containing gas and causes the growth of SWNT. Thus, the diameter distribution of the SWNTs can be controlled by using catalyst particles having a narrow range of diameters.

III. The Catalyst

The catalyst composition can be any catalyst composition known to those of skill in the art. The catalyst particles themselves can be of any material that exhibits ferri- or ferromagnetism. Conveniently, the particles will be of a magnetic metal or alloy, such as, for example, iron, iron oxide, or a ferrite such as cobalt, nickel, chromium, yttrium, hafnium or manganese. The particles useful according to the invention will preferably have an average overall particle size of up to 50 nm to about 1 µm, although, in general, the particle sizes for individual particles can be from about 400 nm to about 1 µm. The catalyst particles are preferably at least single domain size, generally less than about 2 nm.

The function of the catalyst when used in the carbon nanotube growth process is to decompose the carbon precursors and aid the deposition of ordered carbon. The methods and processes of the present invention preferably use metal nanoparticles as the metallic catalyst. The metal or combination of metals selected as the catalyst can be processed to obtain the desired particle size and diameter distribution. The metal nanoparticles can then be separated by being supported on a material suitable for use as a support during synthesis of carbon nanotubes using the metal growth catalysts described below. The particle size of the catalyst particle, before and after being supported, can be determined using superconducting quantum interference device (SQUID) magnetometer. As known in the art, the support can be used to separate the catalyst particles from each other thereby providing the catalyst materials with greater surface area in the catalyst composition. Such support materials include powders of crystalline silicon, polysilicon, silicon nitride, tungsten, magnesium, aluminum and their oxides, preferably aluminum oxide, silicon oxide, magnesium oxide, or titanium dioxide, or combination thereof, optionally modified by addition elements, are used as support powders. Silica, alumina and other materials known in the art may be used as support, preferably alumina is used as the support.

The metal catalyst can be selected from a Group V metal, such as V or Nb, and mixtures thereof, a Group VI metal including Cr, W, or Mo, and mixtures thereof, VII metal, such as, Mn, or Re, Group VIII metal including Co, Ni, Ru, Rh, Pd, Os, Ir, Pt, and mixtures thereof, or the lanthanides, such as Ce, Eu, Er, or Yb and mixtures thereof, or transition metals such as Cu, Ag, Au, Zn, Cd, Sc, Y, or La and mixtures thereof. Specific examples of mixture of catalysts, such as bimetallic catalysts, which may be employed by the present invention include Co—Cr, Co—W, Co—Mo, Ni—Cr, Ni—W, Ni—Mo, Ru—Cr, Ru—W, Ru—Mo, Rh—Cr, Rh—W, Rh—Mo, Pd—Cr, Pd—W, Pd—Mo, Ir—Cr, Pt—Cr, Pt—W, and Pt—Mo. Preferably, the metal catalyst is iron, cobalt, nickel, molybdeum, or a mixture thereof, such as Fe—Mo, Co—Mo and Ni—Fe—Mo.

The metal, bimetal, or combination of metals are used to prepare metal nanoparticles having defined particle size and diameter distribution. The metal nanoparticles can be prepared using the literature procedure described in Harutyunyan et al., NanoLetters 2, 525 (2002). Alternatively, the catalyst nanoparticles can be prepared by thermal decomposition of the corresponding metal salt added to a passivating salt, and the temperature of the solvent adjusted to provide the metal nanoparticles, as described in the co-pending and co-owned U.S. patent application Ser. No. 10/304,316, or by any other method known in the art. The particle size and diameter of the metal nanoparticles can be controlled by using the appropriate concentration of metal in the passivating solvent and by controlling the length of time the reaction is allowed to proceed at the thermal decomposition temperature. The metal salt can be any salt of the metal, and can be selected such that the melting point of the metal salt is lower than the boiling point of the passivating solvent. Thus, the metal salt contains the metal ion and a counter ion, where the counter ion can be nitrate, nitride, perchlorate, sulfate, sulfide, acetate, halide, oxide, such as methoxide or ethoxide, acetylacetonate, and the like. For example, the metal salt can be iron acetate ($FeAc_2$), nickel acetate ($NiAc_2$), palladium acetate ($PdAc_2$), molybdenum acetate ($MoAc_3$), and the like, and combinations thereof. The melting point of the metal salt is preferably about 5° C. to 50° C. lower than the boiling point, more preferably about 5° C. to about 20° C. lower than the boiling point of the passivating solvent. The solvent can be an ether, such as a glycol ether, 2-(2-butoxyethoxy)ethanol, $H(OCH_2CH_2)_2O(CH_2)_3CH_3$, which will be referred to below using the common name dietheylene glycol mono-n-butyl ether, and the like.

Metal nanoparticles having an average particle size of about 0.01 nm to about 20 nm, more preferably about 0.1 nm to about 3 nm and most preferably about 0.3 nm to 2 nm can be prepared. The metal nanoparticles can thus have a particle size of 0.1, 1, 2, 3, 4, 5, 6, 7, 8, 9, or 10 nm, and up to about 20 nm. In another aspect, the metal nanoparticles can have a range of particle size, or diameter distribution. For example, the metal nanoparticles can have particle sizes in the range of about 0.1 nm and about 5 nm in size, about 3 nm and about 7 nm in size, or about 5 nm and about 11 nm in size.

The size and distribution of metal nanoparticles produced can be verified by any suitable method. One method of verification is transmission electron microscopy (TEM). A suitable model is the Phillips CM300 FEG TEM that is commercially available from FEI Company of Hillsboro, Oreg. In order to take TEM micrographs of the metal nanoparticles, 1 or more drops of the metal nanoparticle/passivating solvent solution are placed on a carbon membrane grid or other grid suitable for obtaining TEM micrographs. The TEM apparatus is then used to obtain micrographs of the nanoparticles that can be used to determine the distribution of nanoparticle sizes created.

In another method, the size of the nanoparticles and their distribution can be determined using SQUID. SQUID magnetometers are commercially available from companies such as Biomagnetic Technologies Inc., San Diego, Calif. and Siemens AG of Germany, and include both single and multi-channel devices that are capable of detecting magnetic fields at plurality of locations simultaneously. SQUID magnetometers generally comprise a superconducting pick up coil system and a detector system (the SQUID) which itself comprises one or two Josephson junctions inserted into a loop of superconducting wire. The magnetic flux within such loops is quantized and changes in the magnetic field experienced by the pick up coils cause a measurable change in the current flowing through the detector. The SQUID magnetometers are capable of measuring very low magnetic fields, for example, as low as $10^{-14}$ Tesla. The technique thus finds use in a variety of fields.

The magnetic properties of the catalyst particles, either beginning of the synthesis process or at the end of the process, can be measured using SQUID. The details of the operation of SQUID are known to those skilled in the art, and can be found in C. Hilbert and J. Clarke, Journal of Low Temperature Physics 61, 237 and 261 (1985). The signals involved in detecting the electric induction phenomenon of the present invention can be small. Hence, the reduction in the noise level in the system can be advantageous, and can be achieved by optionally conducting the measurements at reduced temperature, such as in a liquid helium environment to reduce thermally induced noise levels.

It has been found that the magnetization curves for catalysts having particle sizes of less than about 1.5 nm is paramagnetic, and the magnetization curves for particle sizes greater than about 2 nm is superparamagnetic, and greater than 4 nm is ferromagnetic Thus, in one aspect, the evolution of magnetic properties of the catalyst particles can be used for synthesis of the catalyst particles with the desired sized. The metal/support material molar ratio can be varied if the magnetization curves observed in SQUID are not the same as the magnetization curves expected for the desired particle sizes. The ratio can be fixed if the magnetization curves observed in SQUID are similar to the magnetization curves expected for the desired particle sizes.

Thus, if the desired average particle size is about 2 nm or greater, such as between 1 nm and about 3 nm, then the variation of the metal/support material ratio is continued until the SQUID measurements provide magnetization curves indicating that the particles are superparamagnetic. If the desired average particle size is less than about 1 nm, such as 0.5 nm, 0.8 nm, 1 nm, and the like, then the variation of the metal/support material ratio is continued until the SQUID measurements provide magnetization curves indicating that the particles are paramagnetic.

The metal nanoparticles, such as those formed by thermal decomposition described in detail above, and, optionally characterized by SQUID, can then be supported on solid supports. The solid support can be silica, alumina, MCM-41, MgO, $ZrO_2$, aluminum-stabilized magnesium oxide, zeolites, or other oxidic supports known in the art, and combinations thereof. For example, $Al_2O_3$—$SiO_2$ hybrid support could be used. Preferably, the support is aluminum oxide ($Al_2O_3$) or silica ($SiO_2$). The oxide used as solid support can be powdered thereby providing small particle sizes and large surface areas. The powdered oxide can preferably have a particle size between about 0.01 µm to about 100 µm, more preferably about 0.1 µm to about 10 µm, even more preferably about 0.5 µm to about 5 µm, and most preferably about 1 µm to about 2 µm. The powdered oxide can have a surface area of about 50 to about 1000 $m^2/g$, more preferably a surface area of about 200 to about 800 $m^2/g$. The powdered oxide can be freshly prepared or commercially available.

In one aspect, the metal nanoparticles are supported on solid supports via secondary dispersion and extraction. Secondary dispersion begins by introducing particles of a powdered oxide, such as aluminum oxide ($Al_2O_3$) or silica ($SiO_2$), into the reaction vessel after the thermal decomposition reaction. A suitable $Al_2O_3$ powder with 1-2 µm particle size and having a surface area of 300-500 $m^2/g$ is commercially available from Alfa Aesar of Ward Hill, Mass., or Degussa, N.J. Powdered oxide can be added to achieve a desired weight ratio between the powdered oxide and the initial amount of metal used to form the metal nanoparticles. Typically, the weight ratio can be between about 10:1 and about 15:1. For example, if 100 mg of iron acetate is used as the starting material, then about 320 to 480 mg of powdered oxide can be introduced into the solution. The weight ratio of metal nanoparticles to powdered oxide can be between about 1:10 and 1:15, such as, for example, 1:11, 1:12, 2:25, 3:37, 1:13, 1:14, and the like.

As will be apparent to those of skill in the art, the catalyst thus prepared can be stored for later use. In another aspect, the metal nanoparticles can be previously prepared, isolated from the passivating solvent, and purified, and then added to a powdered oxide in a suitable volume of the same or different passivating solvent. The metal nanoparticles and powdered oxide can be homogenously dispersed, extracted from the passivating solvent, and processed to increase the effective surface area as described above. Other methods for preparing the metal nanoparticle and powdered oxide mixture will be apparent to those skilled in the art.

Three different groups of iron catalysts supported on alumina were prepared and their magnetization curves obtained using SQUID, are shown in FIG. 1a, b, c. Catalyst particles on alumina support powder (Fe:$Al_2O_3$=1:15 mol:mol), with the in-situ formation of the iron nanoparticles inside the pores of the support, and having average particle size of less than about 2 nm exhibit showed paramagnetic behavior at room temperature as well as lower temperature of 5 K (FIGS. 1a and 1g). In contrast, catalyst particles on support powders having mean diameters of greater than or equal to about 2 nm showed superparamagnetic behavior at room temperature (FIG. 1b, c).

The metal nanoparticles thus formed can be used as a growth catalyst for synthesis of carbon nanotubes, nanofibers, and other one-dimensional carbon nanostructures by a chemical vapor deposition (CVD) process.

IV. Carbon Precursors

The carbon nanotubes can be synthesized using carbon precursors, such as carbon containing gases. In general, any carbon containing gas that does not pyrolyze at temperatures up to 800° C. to 1000° C. can be used. Examples of suitable carbon-containing gases include carbon monoxide, aliphatic hydrocarbons, both saturated and unsaturated, such as methane, ethane, propane, butane, pentane, hexane, ethylene, acetylene and propylene; oxygenated hydrocarbons such as acetone, and methanol; aromatic hydrocarbons such as benzene, toluene, and naphthalene; and mixtures of the above, for example carbon monoxide and methane. In general, the use of acetylene promotes formation of multi-walled carbon nanotubes, while CO and methane are preferred feed gases for formation of single-walled carbon nanotubes. The carbon-containing gas may optionally be mixed with a diluent gas such as hydrogen, helium, argon, neon, krypton and xenon or a mixture thereof.

V. Synthesis of Carbon Nanotubes

The methods and processes of the invention provide for the synthesis of SWNTs with a narrow distribution of diameters. The narrow distribution of carbon nanotube diameters is obtained by activating small diameter catalyst particles preferentially during synthesis by selecting the lowest eutectic point as the reaction temperature.

In one aspect of the invention, the metal nanoparticles supported on powdered oxides can be contacted with the carbon source at the reaction temperatures according to the literature methods described in Harutyunyan et al., NanoLetters 2, 525 (2002). Alternatively, the metal nanoparticles supported on the oxide powder can be aerosolized and introduced into the reactor maintained at the reaction temperature. Simultaneously, the carbon precursor gas is introduced into the reactor. The flow of reactants within the reactor can be controlled such that the deposition of the carbon products on the walls of the reactor is reduced. The carbon nanotubes thus produced can be collected and separated.

The metal nanoparticles supported on the oxide powder can be aerosolized by any of the art known methods. In one method, the supported metal nanoparticles are aerosolized using an inert gas, such as helium, neon, argon, krypton, xenon, or radon. Preferably argon is used. Typically, argon, or any other gas, is forced through a particle injector, and into the reactor. The particle injector can be any vessel that is capable of containing the supported metal nanoparticles and that has a means of agitating the supported metal nanoparticles. Thus, the catalyst deposited on a powdered porous oxide substrate can be placed in a beaker that has a mechanical stirrer attached to it. The supported metal nanoparticles can be stirred or mixed in order to assist the entrainment of the catalyst in the transporter gas, such as argon.

Thus, the nanotube synthesis generally occurs as described in the co-pending and coowned application U.S. Ser. No. 10/727,707, filed on Dec. 3, 2003. An inert transporter gas, preferably argon gas, is generally passed through a particle injector. The particle injector can be a beaker or other vessel containing the growth catalyst supported on a powdered porous oxide substrate. The powdered porous oxide substrate in the particle injector can be stirred or mixed in order to assist the entrainment of the powdered porous oxide substrate in the argon gas flow. Optionally, the inert gas can be passed through a drying system to dry the gas. The argon gas, with the entrained powdered porous oxide, can then be passed through a pre-heater to raise the temperature of this gas flow to about 400° C. to about 500° C. The entrained powdered porous oxide is then delivered to the reaction chamber. A flow of methane or another carbon source gas and hydrogen is also delivered to the reaction chamber. The typical flow rates can be 500 sccm for argon, 400 sccm for methane, and 100 sccm for He. Additionally, 500 sccm of argon can be directed into the helical flow inlets to reduce deposition of carbon products on the wall of the reaction chamber. The reaction chamber can be heated to between about 300° C. and 900° C. during reaction using heaters. The temperature is preferably kept below the decomposition temperature of the carbon precursor gas. For example, at temperatures above 1000° C., methane is known to break down directly into soot rather than forming carbon nanostructures with the metal growth catalyst. Carbon nanotubes and other carbon nanostructures synthesized in reaction chamber can then be collected and characterized.

In another aspect, a range of particle diameters within the distribution of the catalyst sizes can be selected for the synthesis of SWNTs by selecting the temperature at which the production of the SWNTs is carried out. The synthesis of the catalyst nanoparticles typically results in a Gaussian distribution of particle sizes. Thus, for example, the synthesis of 1 nm Fe catalysts can have a distribution of particle diameters ranging from about 0.01 nm to about 5 nm, with the majority of particle diameters centering around 1 nm. Normally, the catalysts would be further processed to obtain a tighter distribution of catalyst particle sizes. In contrast, the present methods and process allow for the selection of a narrow distribution of catalyst particles without further processing. In the inventive methods, the reaction temperature can be selected such that it is near or above the eutectic point and so that catalyst particle sizes smaller than the mean are first used for the synthesis of SWNTs. As these catalysts become exhausted, the reaction temperature can be raised such that catalyst particles of sizes near the mean are used for the synthesis of SWNTs. The reaction temperature can be further raised such that catalyst particles of sized near the upper range are used for the synthesis of SWNTs. The methods and processes of the present invention thus have the advantage that the particle size of the catalyst need not be tightly controlled during the synthesis of the catalyst, thereby providing for economical production of SWNTs.

In one aspect of the invention, the diameter distribution of the synthesized SWNTs is substantially uniform. Thus, about 90% of the SWNTs have a diameter within about 25% of the mean diameter, more preferably, within about 20% of the mean diameter, and even more preferably, within about 15% of the mean diameter. Thus, the diameter distribution of the synthesized SWNTs can be about 10% to about 25% within the mean diameter, more preferably about 10% to about 20% of the mean diameter, and even more preferably about 10% to about 15% of the mean diameter.

Figure 2:
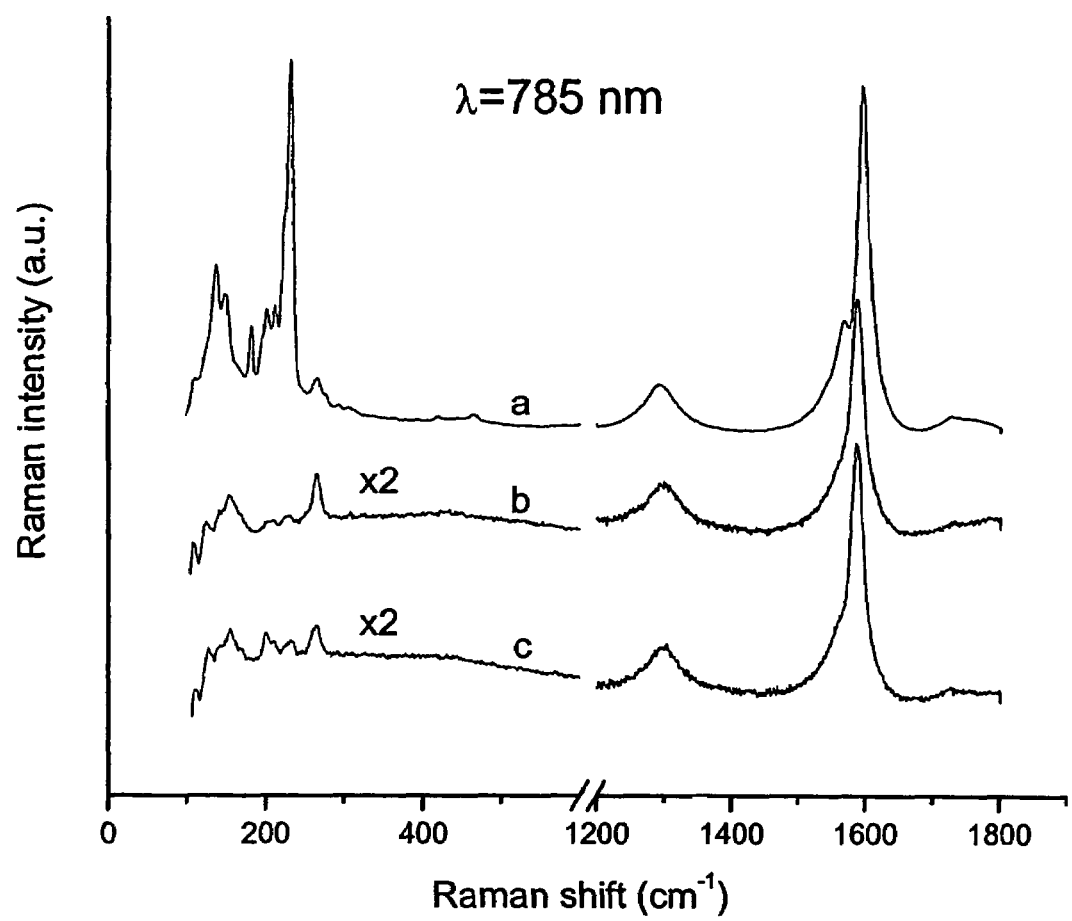
FIG. 2 depicts Raman spectra of carbon SWNTs ($\lambda$=785 nm excitation) grown using Fe nanoparticles with mean diameters: a) less than 1 nm, b) about 5 nm and c) about 9 nm.

Carbon SWNTs were synthesized with the yields ranging from about 4 wt % to about 15 wt % (wt % carbon relative to the iron/alumina catalyst). Analysis of transmission electron microscopy (TEM) images of SWNTs produced by using 9 nm iron nanoparticles showed bundles with an average diameter of about 10 nm to about 15 nm. Analysis of TEM images of SWNTs produced by using 5 nm iron catalyst showed average diameter of about 7 nm to about 12 nm. Analysis of TEM images of SWNTs produced by using 1 nm iron nanoparticles showed bundles with diameter about 5 nm to about 10 nm as well as many individual SWNTs. In all cases, a broad distribution of SWNTs diameters from 0.8 to 2 nm was observed. The diameters estimated from TEM were confirmed from the radial breathing modes observed by Raman Spectroscopy spectra, using six different laser excitations ($\lambda$=1064; 785; 614, 532, 514 and 488 nm). In FIG. 2, Raman spectra of carbon SWNTs is shown for $\lambda$=785 nm laser excitation.

The magnetic properties of the catalyst nanoparticles were also measured after the SWNTs growth using SQUID (FIG. 3d, e, f). After the SWNTs growth, the catalyst with mean diameter less than 1 nm, showed superparamagnetic properties (FIG. 3d) at both room temperature and at 5 K. The catalysts with the mean diameters of 5 and 9 nm showed ferromagnetism, even at room temperature. The larger particles (9 nm) showed larger coercive forces after SWNTs growth (Hc=145 Gs at 300 K) compared to the catalysts having smaller particle sizes (Hc=43 Gs and Hc=0 Gs at 300 K in FIG. 3d, e).

The correlation between the magnetic properties and particle diameter for ultrafine metal powders has always studied. In particular, the coercivity of the metal powders ($H_c$) has been found to depend strongly on particle size (Gangopadhyay et al. Phys. Rev. B 45, 9778 (1992)). According to the model developed by Kneller and Luborsky (J. Appl. Phys. 34, 656 (1963)), the decrease in $H_c$ with decreasing particle size, is due to the thermal effects observed in particles with a size below the single domain particle, which for iron is approximately 20 nm. The following expression for the coercivity ($H_c$) vs. temperature (T) is employed:

$$H_c = H_c^\circ [1-(25\ kT/KV)^{1/2}] \quad (1)$$

where K is the bulk anisotropy constant, V is the volume of particles and $H_c^\circ$ is the zero-temperature coercivity. At room temperature, the smaller particles have smaller coercive forces. Therefore, without being bound to any theory, the increase of coercive forces of the catalysts and the phase transitions from paramagnetic to superparamagnetic and superparamagnetic to ferromagnetic after nanotubes growth, can be attributed to the increase in the diameter of catalyst particles. Thus, the growth of nanotubes may be accompanied by the migration and liquefaction of iron catalyst nanoparticles that results in the formation of larger particles.

The Raman spectra of SWNTs has three major peaks, which are the G-band at about 1590 cm$^{-1}$, D-band at about 1350 cm$^{-1}$, and the Radial breathing mode (RBM) at about 100-300 cm$^{-1}$, RBM frequency is proportional to an inverse of the diameter of SWNTs and can thus be used to calculate the diameter of the SWNT. Normally, a red shift in RBM peak corresponds to an increase in the mean diameter of SWNTs. The tangential mode G-band related to the Raman-allowed phonon mode $E_{2g}$ can be a superposition of two peaks. The double peak at about 1593 and 1568 cm$^{-1}$ has been assigned to semiconductor SWNTs, while the broad Breit-Wigner-Fnao line at about 1550 cm$^{-1}$ has been assigned to metallic SWNTs. Thus, G-band offers a method for distinguishing between metallic and semiconducting SWNTs. The D-band structure is related to disordered carbon, the presence of amorphous carbon, and other defects due to the sp$^2$-carbon network. The ratio of the G-band to D-band in the Raman spectra ($I_G$:$I_D$ or G/D ratio) of SWNTs can be used as an index to determine the purity and quality of the SWNTs produced. Preferably, $I_G$:$I_D$ is about 1 to about 500, preferably about 5 to about 400, more preferably greater than about 10.

Using the methods and processes of the invention, SWNTs with $I_G$:$I_D$ of about 10 to about 40 can be manufactured. The quality of the SWNTs depends on the particle size of the catalyst. The particle sizes of the catalyst particles can be determined using SQUID. The synthesis process can be continued until the particle size distribution of the catalysts is within a narrow range. The use of catalyst particles thus prepared provides SWNTs of greater purity and quality.

The carbon nanotubes and nanostructures produced by the methods and processes described above can be used in applications that include Field Emission Devices, Memory devices (high-density memory arrays, memory logic switching arrays), Nano-MEMs, AFM imaging probes, distributed diagnostics sensors, and strain sensors. Other key applications include: thermal control materials, super strength and light weight reinforcement and nanocomposites, EMI shielding materials, catalytic support, gas storage materials, high surface area electrodes, and light weight conductor cable and wires, and the like.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Preparation of the Supported Catalyst

Catalysts were prepared by impregnating support materials in metal salt solutions. Three different groups of catalyst particles were synthesized and used for growing SWNTs by CVD. Two groups of narrow dispersed iron catalysts, with average diameters of about 5 nm and about 9 nm, were obtained by thermal decomposition of iron acetate in glycol solution under nitrogen atmosphere. The reaction time and iron acetate/glycol ratio were changed to control the sizes of nanoparticles. In a typical procedure, $FeAc_2$ in methanol was used at a molar ratio of $Fe:Al_2O_3$ of 1:15. Under a nitrogen atmosphere, $FeAc_2$ was added to dietheylene glycol mono-n-butyl ether in the molar ratio of 1 mM:20 mM. The reaction mixture was mixed under the nitrogen atmosphere using a magnetic stir bar, and heated under reflux for 90 minutes. The reaction mixture was then cooled to room temperature, and $Al_2O_3$ (15 mM) was added at once (molar ratio $Fe:Al_2O_3$=1:15). The reaction solution was stirred at room temperature for 15 minutes, and then heated to 150° C. for 3 hours. The reaction was cooled to 90° C. while flowing a stream of $N_2$ over the mixture to remove the solvent. A black film formed on the walls of the reaction flask. The black film was collected and ground with an agate mortar to obtain a fine black powder.

The third group of catalyst was prepared by a common wet catalyst method, using iron (II) sulfate and alumina support powder (molar ratio $Fe:Al_2O_3$=1:15), with the in-situ formation of the iron nanoparticles inside the pores of the support as described in A. R. Harutyunyan, B. K. Pradhan, U. J. Kim, G. Chen, and P. C. Eklund, NanoLetters 2, 525 (2002).

The magnetization curves of the three groups of catalysts prepared above were obtained using SQUID, and are shown in FIGS. 1a, b, and c.

Example 2

Synthesis of Carbon Nanotubes

Carbon nanotubes were synthesized by using the experimental setup described in Harutyunyan et al., NanoLetters 2, 525 (2002). CVD growth of SWNTs, with the three different catalysts, used methane as a carbon source (T=800° C., methane gas flow rate 60 sccm). In all cases, carbon SWNTs were successfully synthesized with the yields ~4, 7 and 15 wt % (wt % carbon relative to the iron/alumina catalyst) for the catalysts with the diameters 9, 5 nm and for catalyst made by of iron-sulfate decomposition, respectively. Analysis of many transmission electron microscopy (TEM) images of SWNTs produced by using 9 nm iron nanoparticles showed bundles with an average diameter of ~10-15 nm, while in case of 5 nm iron catalyst was ~7-12 nm. The iron-sulfate decomposed catalyst showed bundles with diameter ~5-10 nm as well as many individual SWNTs. In all cases, a distribution of SWNTs diameters from 0.8 to 2 nm were observed. A Raman spectra of carbon SWNTs using $\lambda$=785 nm laser excitation is shown in FIG. 2. The single-walled carbon nanotubes thus produced were also characterized by TEM.

Example 3

Magnetization Behavior of the Supported Catalyst

Supported catalyst having a molar ratio of $Fe:Al_2O_3$ of 1:14.2 was prepared using the method described in Example 1. The magnetization curve is shown in FIG. 3a. The catalyst thus prepared was subjected to heat treatment by heating at either 200° C. or 800° C. for 15 minutes. The magnetization curves are shown in FIGS. 4a and 4b, respectively. The magnetization curves show that the magnetization behavior of these catalyst changes depending on the temperature used for post-synthesis heat treatment.

Figure 5:
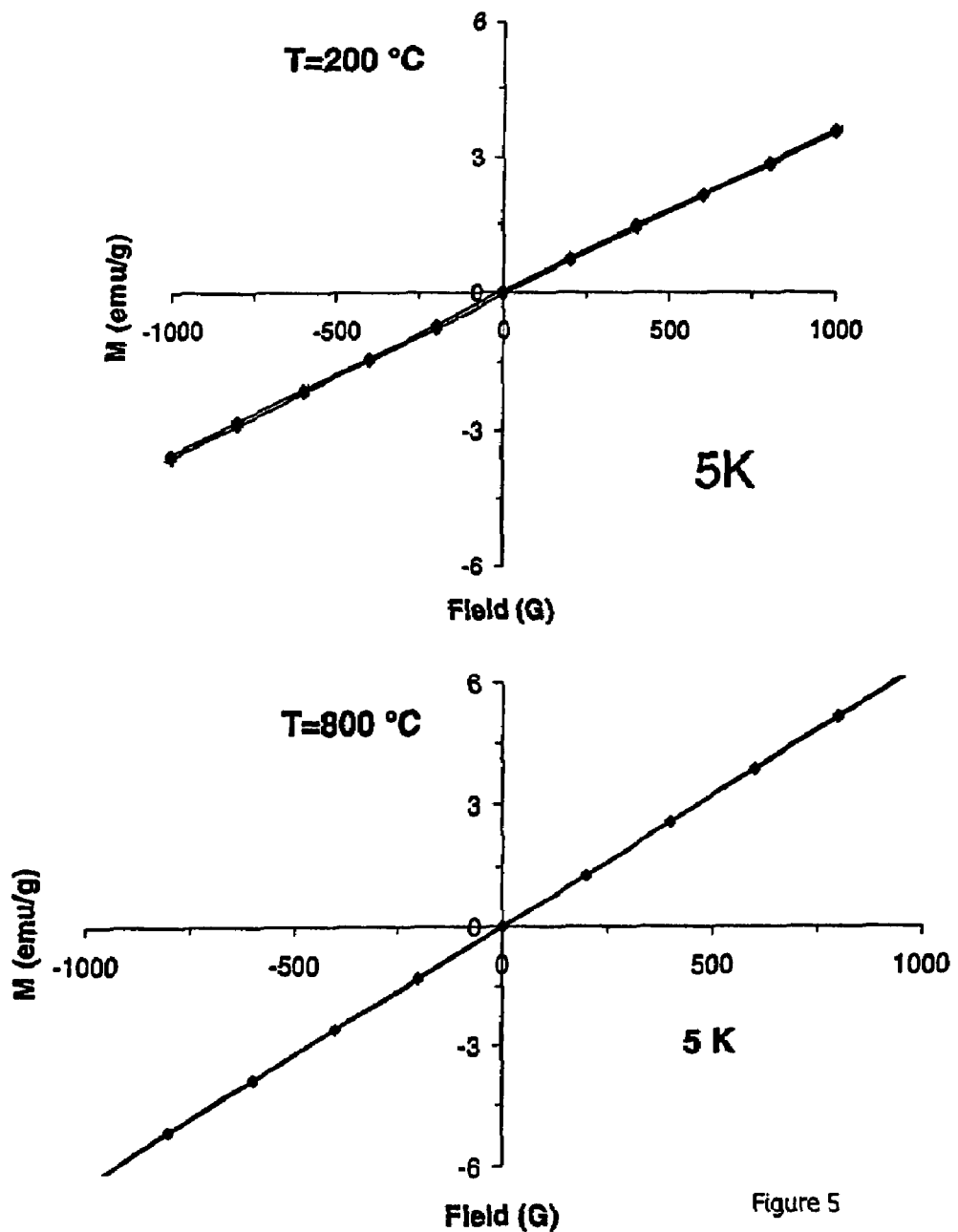
FIG. 5 illustrates the magnetization curves of Fe:$Al_2O_3$ having a ratio is 1:15 after heat treatment at 200° C.

Supported catalyst having a molar ratio of $Fe:Al_2O_3$ of 1:15 (FIG. 3b), prepared in Example 1, was subjected to heat treatment by heating at either 200° C. or 800° C. for 15 minutes. The magnetization curves are shown in FIGS. 5a and 5b, respectively. The magnetization curves show that the magnetization behavior of these catalyst does not change depending on the temperature used for post-synthesis heat treatment.

Figure 6:
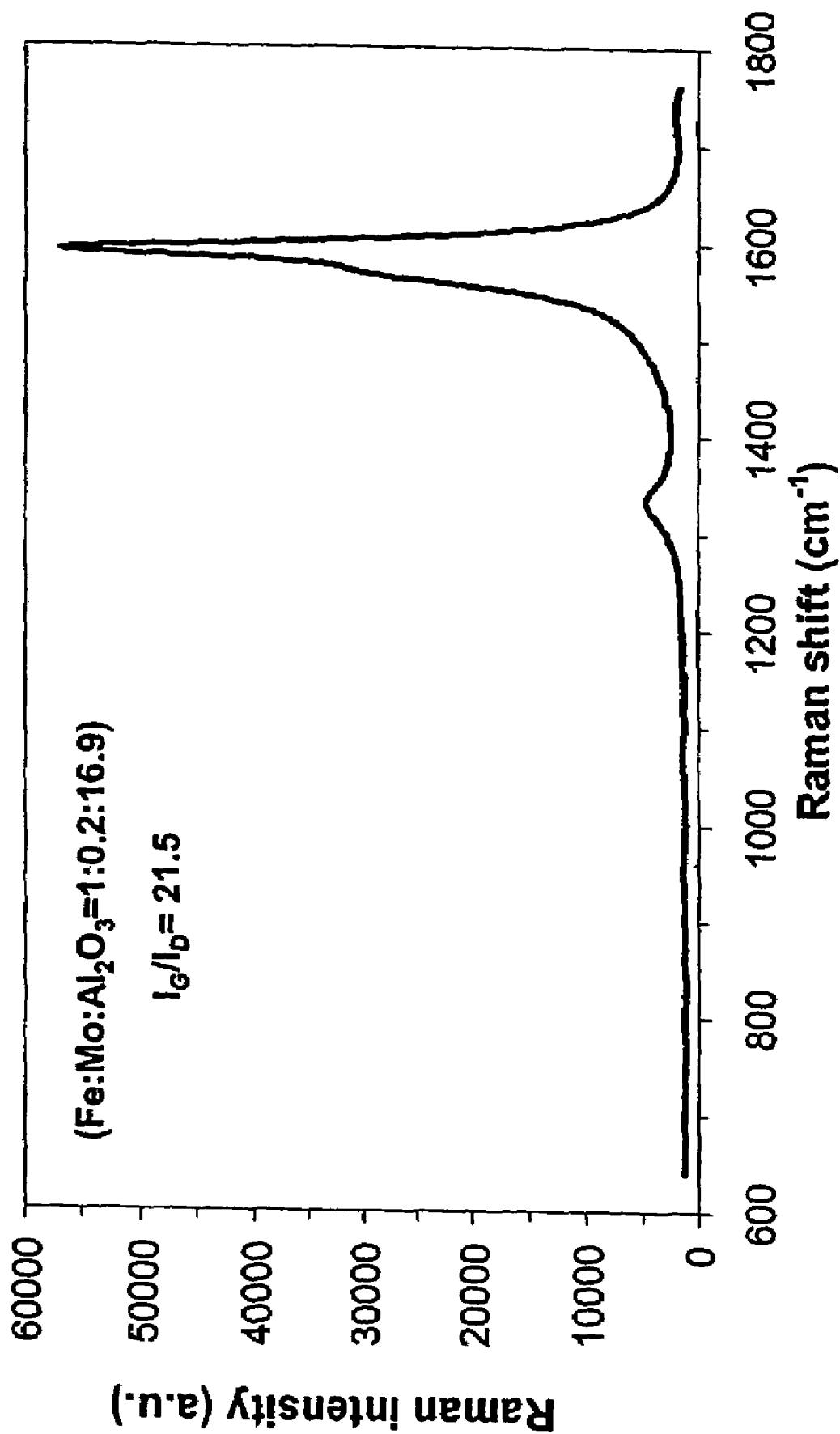
FIG. 6 depicts Raman spectra of carbon SWNTs grown using the optimized catalyst (Fe:Mo:$Al_2O_3$ at a ratio of 1:0.2: 16.9), heat treatment and SWNT synthesis duration.

The magnetization behavior is reflected in the quality of the SWNTs produced. The use of the supported catalyst $Fe:Al_2O_3$ having a molar ratio of 1:14.2 yielded $I_G:I_D$ ratio of 5, whereas, the use of the supported catalyst $Fe:Al_2O_3$ having a molar ratio of 1:14.2 yielded $I_G:I_D$ ratio of 8, and the use of the supported catalyst $Fe:Mo:Al_2O_3$ having a molar ratio of 1:0.2:16.9 yielded $I_G:I_D$ ratio of 21.5 (FIG. 6). Thus, SQUID magnetometer studies of magnetic properties of metal catalyst particles can be used to control the quality of the catalyst. The carbon nanotubes yield and quality are higher when made by using these catalysts.

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

We claim:

1. A method for determining the average particle size of a metal catalyst, the method comprising:
   obtaining a magnetization curve of the metal catalyst using SQUID magnetometer, wherein the catalyst is on a powdered oxide support, wherein the powdered oxide is selected from the group consisting of $Al_2O_3$, $SiO_3$, MgO and zeolites; and determining the average particle size from the magnetization curve.

2. The method of claim 1, wherein the catalyst is selected from the group consisting of a Group V metal, a Group VI metal, a Group VII metal, a Group VIII metal, a lanthanide, and a transition metal, or mixtures thereof.

3. The method of claim 2, wherein the catalyst is selected from the group consisting of Fe, V, Nb, Cr, W, Mo, Mn, Re, Co, Ni, Ru, Rh, Pd, Os, Ir, Pt, Ce, Eu, Er, Yb, Ag, Au, Zn, Cd, Sc, Y, or La or mixtures thereof.

4. The method of claim 3, wherein the catalyst is Cr, Fe, Ni, Co, Y, Hf, or Mo, and combinations thereof.

5. The method of claim 2, wherein the catalyst is selected from the group consisting of Co—Cr, Co—W, Co—Mo, Ni—Cr, Ni—W, Ni—Mo, Ru—Cr, Ru—W, Ru—Mo, Rh—Cr, Rh—W, Rh—Mo, Pd—Cr, Pd—W, Pd—Mo, Ir—Cr, Pt—Cr, Pt—W, and Pt—Mo.

6. The method of claim 2, wherein the catalyst is selected from the group consisting Fe—Mo, Co—Mo and Ni—Fe—Mo.

7. The method of claim 1, wherein the powdered oxide is $Al_2O_3$.

8. The method of claim 1, wherein the catalyst and the support are in a ratio of about 1:1 to about 1:50.

9. The method of claim 8, wherein the ratio is about 1:10 to about 1:20.

10. The method of claim 1, wherein the magnetization curve is paramagnetic or superparamagnetic.

11. The method of claim 10, wherein the magnetization curve is paramagnetic when particle size of the catalyst is less than about 2 nm.

12. The method of claim 10, wherein the magnetization curve is superparamagnetic when the particle size of the catalyst is greater than about 5 nm.

* * * * *

UNITED STATES PATENT AND TRADEMARK OFFICE
CERTIFICATE OF CORRECTION

PATENT NO. : 7,719,265 B2  
APPLICATION NO. : 10/992275  
DATED : May 18, 2010  
INVENTOR(S) : Avetik R. Harutyunyan et al.

Page 1 of 1

It is certified that error appears in the above-identified patent and that said Letters Patent is hereby corrected as shown below:

Column 2, line 44, delete "$SiO_3$", insert --$[SiO_2]$--.
Column 2, line 59, delete "$SiO_3$", insert --$[SiO_2]$--.
Column 3, line 8, delete "$SiO_3$", insert --$[SiO_2]$--.
Column 12, line 66, delete "$SiO_3$", insert --$[SiO_2]$--.

Signed and Sealed this
Fifteenth Day of February, 2011

David J. Kappos
*Director of the United States Patent and Trademark Office*